(12) United States Patent
De Simone

(10) Patent No.: US 8,697,051 B2
(45) Date of Patent: *Apr. 15, 2014

(54) COMPOSITION COMPRISING ALKALINE SPHINGOMYELINASE FOR USE AS A DIETETIC PREPARATION, FOOD SUPPLEMENT OR PHARMACEUTICAL PRODUCT

(75) Inventor: Claudio De Simone, Ardea (IT)

(73) Assignee: VSL Pharmaceuticals Inc., Rome (IT)

( * ) Notice: Subject to any disclaimer, the term of this patent is extended or adjusted under 35 U.S.C. 154(b) by 1186 days.

This patent is subject to a terminal disclaimer.

(21) Appl. No.: 11/105,592

(22) Filed: Apr. 14, 2005

(65) Prior Publication Data

US 2005/0186190 A1    Aug. 25, 2005

Related U.S. Application Data

(63) Continuation-in-part of application No. 10/964,770, filed on Oct. 15, 2004, now abandoned, which is a continuation of application No. 09/960,652, filed on Sep. 24, 2001, now abandoned, which is a continuation of application No. PCT/IT00/00230, filed on Jun. 7, 2000.

(30) Foreign Application Priority Data

Jun. 19, 1999    (IT) ................... RM99A0376

(51) Int. Cl.
*A01N 63/00* (2006.01)
*A01N 63/02* (2006.01)

(52) U.S. Cl.
USPC .............. 424/93.4; 424/93.45; 424/93.6

(58) Field of Classification Search
USPC ..................... 435/252.2, 252.9; 424/94.8
See application file for complete search history.

(56) References Cited

U.S. PATENT DOCUMENTS

| | | | | |
|---|---|---|---|---|
| 4,071,037 | A | * | 1/1978 | Scheinberg ............... 131/334 |
| 4,085,228 | A | | 4/1978 | Reinbold et al. |
| 4,158,607 | A | | 6/1979 | Kalinowski et al. |
| 4,524,136 | A | | 6/1985 | Lee et al. |
| 5,716,615 | A | | 2/1998 | Cavaliere Vesely et al. |
| 5,851,782 | A | | 12/1998 | Hannun et al. |
| 5,912,152 | A | | 6/1999 | Hara et al. |
| 6,572,854 | B1 | * | 6/2003 | De Simone ............. 424/93.45 |

FOREIGN PATENT DOCUMENTS

| | | |
|---|---|---|
| FR | 2 729 079 | 7/1996 |
| GB | 2 037 160 | 7/1980 |
| JP | 63-216813 | 9/1988 |
| WO | WO 98/00035 | 1/1998 |
| WO | WO 98/22082 | 5/1998 |
| WO | WO 99/42568 | 8/1999 |

OTHER PUBLICATIONS

Nilson et al. "Alkaline sphingomyelinase and ceramidases of the gastrointestinal tract". Chemistry and Physics of Lipids. 1999, 102:97-105.*
Lin et al. "Identification of neutral and acidic sphingomyelinase in *Helicobacter pylori*". FEBS Letters. 1998, 423:249-253.*
Hetland et al. "Phospholipase C from *Bacillus cereus* has sphingomyelinase activity". Scand. J. Clin. Invest. 1982, 42:57-61.*
Sjoqvist et al, "Chronic Colitis with Dysplasia is Associated With a Reduction of Alkaline Sphingomyelinase Activity", Gastroenterology 116(4 (part 2)):A505 (1999) XP-000971701—Abstract No. G2218.
Rui-Dong Duan, "Sphingomyelin Hydrolysis in the Gut and Clinical Implications in Colorectal Tumorigenesis and Other Gastrointestinal Diseases", Scand. J. Gastroenterol. 33(7):673-683 (1998).
Goni et al "Sphingomyelinases: enzymology and membrane activity", Minireview, FEBS Letters, vol. 531, Issue 1, pp. 38-46, 2002.
Sugimoto et al, Agric. Biol. Chem. 1983, 47(6), 1202-1206.
De Angelis et al. "VSL#3 probiotic preparation has the capacity to hydrolyze gliadin polypeptides responsible for celiac sprue" Biochim. Biophys. Acta 1762:80-93 (2005).
Di Marzio et al. "Detection of alkaline sphingomyelinase activity in human stool: Proposed role as a new diagnositc and prognostic marker of colorectal cancer" Cancer Epidemiol Biomarkers Prev. 14:856-862 (2005).
Duan "Alkaline sphingomyelinase: An old enzyme with novel implications" Biochim. Biophys. Acta 1761:281-291 (2006).
Duan et al. "Alkaline sphingomyelinase activity in rat gastrointestinal tract: Distribution and characteristics" Biochim. Biophys. Acta 1259:49-55 (1995).
Duan et al. "Distribution of alkaline sphingomyelinase activity in human beings and animals" Digestive Dis. Sci. 41:1801-1806 (1996).
Pomerantsev et al. "Phosphatidylcholine-specific phospholipase C and sphingomyelinase activities in bacteria of the *Bacillus cereus* group" Infect. Immun. 71:6591-6606 (2003).
Wu et al. "Intestinal alkaline sphinogomyelinase hydrolyses and inactivates platelet-activating factor by a phospholipase C activity" Biochem. J. 394:299-308 (2006).
Titball et al. "Hemolytic and sphingomyelinase activities of *Clostridium perfringens* alpha-toxin are dependent on a domain homologous to that of an enzyme from the human arachidonic acid pathway" Infec. Immun. 59:1872-1874 (1991).

* cited by examiner

*Primary Examiner* — Vera Afremova
(74) *Attorney, Agent, or Firm* — Gregory P. Einhorn; Gavrilovich, Dodd & Lindsey LLP

(57) ABSTRACT

The invention relates to a composition which, depending on the user, may be taken as a nutritional, dietetic or strictly therapeutic preparation, comprising as its active substance alkaline sphingomyelinase which is capable of preventing or treating various pathological conditions including cancerous processes, inflammatory processes of the intestine, hypercholesterolaemia and infections with *Helicobacter pylori*.

22 Claims, 3 Drawing Sheets

COMPOSITION COMPRISING ALKALINE SPHINGOMYELINASE FOR USE AS A DIETETIC PREPARATION, FOOD SUPPLEMENT OR PHARMACEUTICAL PRODUCT

CROSS REFERENCE TO RELATED APPLICATION

This application is a continuation-in-part of application Ser. No. 10/964,770 filed Oct. 15, 2004 now abandoned which is a continuation of application Ser. No. 09/960,652 filed Sep. 24, 2001 (abandoned) which is a continuation of PCT/IT00/00230 filed Jun. 7, 2000 the disclosures of which are hereby incorporated by reference.

The present invention relates to the use of alkaline sphingomyelinase, preferably of bacterial origin, for the preparation of compositions intended for nutritional, dietetic or strictly therapeutic use, together with the compositions made in this way.

BACKGROUND OF THE INVENTION

Consequently, these compositions may be in the form of and may act as food supplements, dietetic bases or medicinal preparations proper, according to whether they are intended to act as bases or prophylactic treatments or as therapeutic preparations proper, depending on the particular individuals for whom the composition is intended.

Three different types of sphingomyelinase (SMase) have so far been identified.

There is an acidic sphingomyelinase, which is a lysosomal enzyme (with an optimum pH of 4.5-5), deficiency of which causes Niemann-Pick disease, and there is a neutral sphingomyelinase, with an optimum pH of 7.5, for which two iso-forms have been described. One of these iso-forms is located in the cytoplasmic membrane and depends on magnesium, while the other is contained in the cytosol and is independent of cations. Both the acidic and the neutral sphingomyelinase are found in many tissues and cells and are ubiquitous enzymes, regulating numerous cell functions.

The third type is called alkaline sphingomyelinase, because it is mainly active at pH 9. It is independent of magnesium and has been found both in intestinal brush borders and in the bile. Alkaline sphingomyelinase does not occur in the stomach, duodenum or pancreas but it is found in the intestine, especially in the distal part of the jejunum. A marked alkaline sphingomyelinase activity has also been observed in the colon and the rectum. High levels of alkaline sphingomyelinase are also found in the bile, but this seems to be peculiar to human beings. This twofold source of sphingomyelinase makes human beings very efficient in comparison with other creatures as regards the hydrolysis of sphingomyelin (SM) introduced via the diet. It has hitherto been thought that alkaline sphingomyelinase cannot be produced by intestinal bacteria, because no differences have been found between conventional and germ-free animals [see R. D. Duan, *Scand. J. Gastroenterology*, 33 (1998) pp. 673-683].

Apart from the alkaline sphingomyelinase that is present in the intestine and that present in the bile, no other alkaline sphingomyelinases are known that could be used to produce compositions intended for nutritional, dietetic or strictly therapeutic use. Moreover, acidic and neutral sphingomyelinase cannot be employed owing to their differing characteristics (see the following table).

TABLE

| Location | Acidic SMase lysosomes | Neutral SMase cytoplasmic membrane | Alkaline SMase human intestine and bile |
|---|---|---|---|
| Optimum pH | 5.5 | 7.4 | 9 |
| $Mg^{++}$-dependence | No | Yes | No |
| Trypsin resistance | No | No | Yes |
| Thermal stability | <40° C. | — | <50–60° C. |
| Substrate | endocytic SM | membrane SM | SM in food |

The use of sphingomyelinase for cosmetic and dermatological purposes is already known.

Japanese Patent No. 63 216,813 describes cosmetic compositions that contain sphingomyelinase and are intended for counteracting the physiological decrease of this enzyme that occurs in the skin on ageing, and for promoting its transformation into ceramide which, in turn, has a beneficial moisturizing effect on the epidermis.

International Patent Application PCT WO 98/22,082 describes the use of sphingomyelinase for the preparation of dermatological compositions suitable for treating skin disorders such as dermatitis, psoriasis, ichthyosis and similar conditions. Furthermore, this PCT application describes the preparation of sphingomyelinase from strains of Gram-negative bacteria, Gram-positive bacteria and lactic acid bacteria, with clear advantages over the previously known processes, which use the organs of higher animals, such as the brain and liver, as starting materials.

DESCRIPTION OF THE INVENTION

Figure 1:
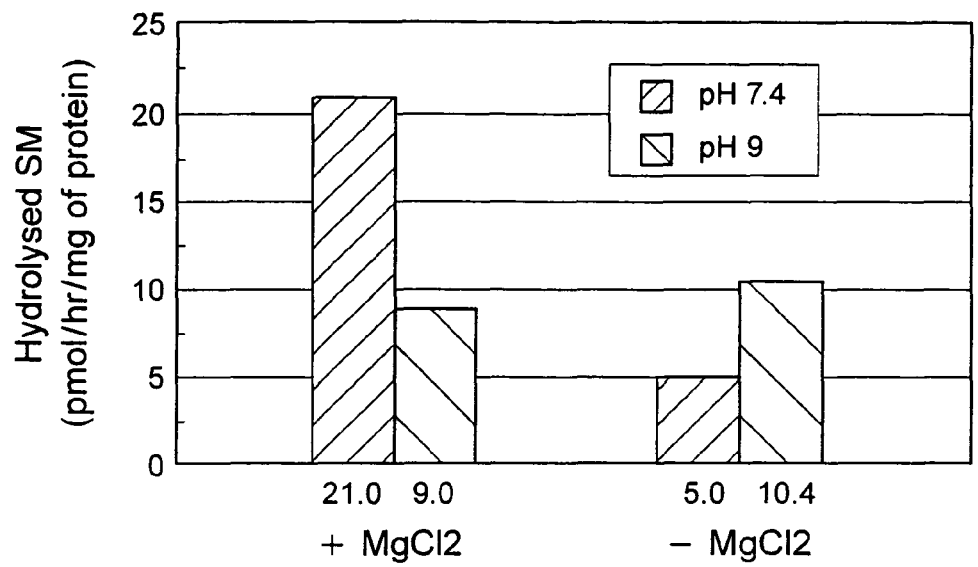
FIG. 1 is a graph showing SMase activity found in *Streptococcus thermophilus*.

It has now been found, surprisingly, that some bacteria possess high levels of alkaline sphingomyelinase, and that their ingestion can be beneficial for the host. These bacteria can be ingested live or in the form of extracts, provided that these are enzymatically active, possibly in combination with other bacteria such as lactic acid bacteria, with SM and/or with foods containing SM.

One of the objects of the present invention is therefore to provide a dietetic, nutrient or pharmaceutical composition that comprises alkaline sphingomyelinase in an amount that is sufficient to exert a dietetic, nutritional or therapeutic effect in an individual who needs it thereby increasing the levels of SMase in the host, particularly humans.

In particular, this composition is suitable for the prevention and/or treatment of disorders connected with intestinal development, cancerous processes, disorders of the immune response, inflammatory and apoptosic processes of the intestine and its associated structures, disorders connected with cholesterol synthesis, disorders due to the hydrophobic nature of the surfaces of the gastrointestinal tract, allergic disorders of the gastro-intestinal tract, disorders relating to digestive processes, inflammatory intestinal diseases, polyposis, in particular familial polyposis, hypercholesterolaemia, infections with *Helicobacter pylori*, disorders of neonatal growth, disorders connected with intestinal homeostasis and diseases of the central and peripheral nervous systems.

The composition is also useful for use in pediatric diets and/or in enteral alimentation. In pediatric diets the composition may be administered, for example, in combination with artificial milk, condensed milk, soybean milk, powdered milk, partially umanized milk and baby foods in general.

There is no need to isolate, purify and characterize alkaline sphingomyelinase from bacteria in order to obtain a therapeutic or beneficial result. The bacteria may be administered per se, either live or lyophilized or sonicated.

The composition preferably contains alkaline sphingomyelinase of bacterial origin, and the bacteria containing the alkaline sphingomyelinase are chosen from amongst Gram-positive bacteria, Gram-negative bacteria and lactic acid bacteria, or from mixtures thereof.

More especially, the alkaline sphingomyelinase of the composition is obtained from lactic acid bacteria, and these are chosen from the group comprising *Lactobacillus acidophilus, Lactobacillus brevis, Lactobacillus buchneri, Lactobacillus casei, Lactobacillus catenaforme, Lactobacillus cellobiosus, Lactobacillus crispatus, Lactobacillus curvatus, Lactobacillus delbrueckii, Lactobacillus fermentum, Lactobacillus jensenii, Lactobacillus leichmannii, Lactobacillus minutus, Lactobacillus plantarum, Lactobacillus rogosae, Lactobacillus salivarius, Bifidobacterium adolescentis, Bifidobacterium angulatum, Bifidobacterium bifidum, Bifidobacterium breve, Bifidobacterium catenulatum, Bifidobacterium dentium, Bifidobacterium eriksonii, Bifidobacterium infantis, Bifidobacterium longum, Bifidobacterium plantarum, Bifidobacterium pseudocatenulatum, Bifidobacterium pseudolongum, Streptococcus lactis, Streptococcus raffinolactis* and *Streptococcus thermophilus*.

The particularly preferred strain amongst these lactic acid bacteria providing alkaline sphingomyelinase is *Lactobacillus brevis* CD2, filed on Feb. 6, 1998 under access No. DSM 11,988 in the German Collection of Micro-organisms and Cell Cultures (DSM) in Braunschweig, Germany ("Deutsche Sammlung von Mikroorganismen und Zellkulturen GmbH") under the Budapest Treaty, or mutants or derivatives thereof.

According to a preferred embodiment of the invention, the lactic acid bacteria providing alkaline sphingomyelinase are used in the composition as live, lyophilized or sonicated bacteria.

The composition preferably contains from $1 \times 10^2$ to $1 \times 10^{13}$ CFUs of lactic acid bacteria per gram of composition.

A particularly preferred composition contains $200 \times 10^9$ *Streptococcus thermophilus*, $150 \times 10^9$ Bifidobacteria and $4 \times 10^9$ *Lactobacillus acidophilus* per gram of composition.

The composition according to the invention can also contain bile acids, in particular ursodeoxycholic acid, pectin, sphingomyelin or its compounds, drugs or foods containing sphingomyelin, arginine deiminase, fatty acids, polyunsaturated fatty acids, non fermented sugars, in particular lactulose, cholesterol inhibitors, ceramidase inhibitors, protease inhibitors, immunomodulators, anti-carcinogenic agents, vitamins, growth factors, surfactants, cereals, fibre, emulsifiers, stabilizers, lipids, antioxidants, preservatives, free-radical neutralizers and/or vaso-protectors.

The composition of the invention can be administered orally as a food supplement or orally or parenterally as a drug.

The invention also relates to the use of alkaline sphingomyelinase preferably of bacterial origin for the preparation of a dietetic, nutrient or pharmaceutical composition suitable for the prevention and/or treatment of disorders connected with intestinal development, cancerous processes, disorders of the immune response, inflammatory and apoptosic processes of the intestine and its associated structures, disorders connected with cholesterol synthesis, disorders due to the hydrophobic nature of the surfaces of the gastrointestinal tract, allergic disorders of the gastro-intestinal tract, disorders relating to digestive processes, inflammatory intestinal diseases, polyposis, in particular familial polyposis, hypercholesterolaemia, infections with *Helicobacter pylori*, disorders of neonatal growth, disorders connected with intestinal homeostasis and diseases of the central and peripheral nervous systems.

This composition is also useful for use in pediatric diets and/or in enteral alimentation. In pediatric diets the composition may be administered, for example, in combination with artificial milk, condensed milk, soybean milk, powdered milk, partially umanized milk and baby foods in general.

The alkaline sphingomyelinase used is preferably of bacterial origin, and the bacteria containing it are chosen from amongst Gram-positive bacteria, Gram-negative bacteria and lactic acid bacteria, or from mixtures thereof.

More especially, the lactic acid bacteria providing alkaline sphingomyelinase used are chosen from the group comprising *Lactobacillus acidophilus, Lactobacillus brevis, Lactobacillus buchneri, Lactobacillus casei, Lactobacillus catenaforme, Lactobacillus cellobiosus, Lactobacillus crispatus, Lactobacillus curvatus, Lactobacillus delbrueckii, Lactobacillus fermentum, Lactobacillus jensenii, Lactobacillus leichmannii, Lactobacillus minutus, Lactobacillus plantarum, Lactobacillus rogosae, Lactobacillus salivarius, Bifidobacterium adolescentis, Bifidobacterium angulatum, Bifidobacterium bifidum, Bifidobacterium breve, Bifidobacterium catenulatum, Bifidobacterium dentium, Bifidobacterium eriksonii, Bifidobacterium infantis, Bifidobacterium longum, Bifidobacterium plantarum, Bifidobacterium pseudocatenulatum, Bifidobacterium pseudolongum, Streptococcus lactis, Streptococcus raffinolactis* and *Streptococcus thermophilus*.

The particularly preferred strain providing alkaline sphingomyelinase amongst these lactic acid bacteria is *Lactobacillus brevis* CD2, filed on Feb. 6, 1998 under access No. DSM 11,988 in the German Collection of Micro-organisms and Cell Cultures (DSM) in Braunschweig, Germany ("Deutsche Sammlung von Mikroorganismen und Zellkulturen GmbH") under the Budapest Treaty, or mutants or derivatives thereof.

According to a preferred embodiment of the invention, the lactic acid bacteria providing alkaline sphingomyelinase are used in the composition as live, lyophilized or sonicated bacteria.

The composition used preferably contains from $1 \times 10^2$ to $1 \times 10^{13}$ CFUs of lactic acid bacteria per gram of composition.

A particularly preferred composition contains $200 \times 10^9$ *Streptococcus thermophilus*, $150 \times 10^9$ Bifidobacteria and $4 \times 10^9$ *Lactobacillus acidophilus* per gram of composition.

The following experiments were carried out to confirm the presence and efficacy of alkaline sphingomyelinase in the bacteria according to the present invention. These experiments involved the detection of alkaline sphingomyelinase, the enzyme responsible for the formation of ceramide in human skin.

Methods

Assay of Acidic, Neutral and Alkaline Sphingomyelinase in Lactic Acid Bacteria and in Intestinal Biopsy Material 10 mg of lyophilized *Streptococcus thermophilus* bacteria were suspended in 500 µl of a buffer containing 50 mM Tris-HCl, pH 7.4, 10 mM $MgCl_2$, 2 mM EDTA, 5 mM DTT, 0.1 mM $Na_3VO_4$, 0.1 mM $Na_2MoO_4$, 30 mM p-nitrophenyl phosphate, 10 mM β-glycerophosphate, 750 mM ATP, 1 µM PMSF, 10 µM leupeptin, 10 µM pepstatin (from Sigma Chemical Co.) and 0.2% Triton X-100 (to assay the activity of neutral SMase) or 500 µl of 0.2% Triton X-100 (to assay the activity of acidic SMase). To assay the alkaline SMase, the bacteria and the (homogenized) intestinal biopsy material were suspended in a 0.25 M sucrose buffer containing 5 mM $MgCl_2$, 0.15 M KCl, 50 mM $KH_2PO_4$, 1 mM PMSF and 1 mM benzamidine (pH 7.4). The samples prepared in this way were then subjected to lysis by sonication (for 30 min during which, 10-sec "on" periods alternated with 10-sec "off" periods), using a Vibracell sonicator (Sonic and Materials Inc., Danbury, Conn.). The sonicated samples were then centrifuged for 30 min at 14,000 rpm at 4° C., the supernatant was removed, and the protein concentration was determined with a kit made by Bio-Rad Laboratories, (Richmond, Calif.).

To determine the neutral SMase, 100 µg of the sample were incubated for 2 hours at 37° C. in a buffer (final volume: 50 µl) containing 50 mM Tris-HCl, 1 mM $MgCl_2$, pH 7.4, and 2.25 µl of [N-methyl-$^{14}$C]-sphingomyelin (SM) (0.2 µCi/ml, specific activity: 56.6 mCi/mmol, Amersham).

To determine the activity of the acidic sphingomyelinase, 100 µg of the bacterial lysate were incubated for 2 hours at 37° C. in a buffer (final volume: 50 µl) containing 250 mM sodium acetate, 1 mM EDTA, pH 5.0, and 2.25 µl of [N-methyl-$^{14}$C]-SM.

To assay the alkaline SMase, the samples were added to 375 µl of Tris-EDTA buffer (pH 9) to a final volume of 0.4 ml, containing 50 mM Tris, 0.15 M NaCl, 2 mM EDTA and a mixture of 3 mM bile salts with a TC:TDC:GC:GCDC molar ratio of 3:2:1.8:1. This mixture of bile salts had been found to possess the highest stimulatory effect on alkaline SMase. The addition of EDTA to the buffer served to inhibit the activity of neutral SMase, which is $Mg^{++}$-dependent with an optimum pH of 7.5. The $^{14}$C-SM was dissolved in ethanol, dried under nitrogen and suspended in the assay buffer, containing a mixture of 3% Triton X-100 and 3 mM bile salts.

The reaction was terminated by the addition of 2 ml of a 2:1 mixture of chloroform and methanol. The phospholipids were extracted and analysed on TLC plates, while the hydrolysis of the SM was quantified by autoradiography and liquid scintillation counting. The SMase present in the sonicated bacteria and in the intestinal biopsy material was expressed as pmol of SM hydrolysed per hour per milligram of protein.

Activity of SMase From *Streptococcus thermophilus*

FIG. 1 shows the activity levels of sphingomyelinase in sonicated lactic acid bacteria. No activity due to acidic SMase was found, but appreciable levels of both neutral and alkaline SMase were observed in the bacterial samples tested under the experimental conditions used (various pH values and with and without $MgCl_2$).

Alkaline SMase Found in Intestinal Biopsy Material

Figure 2:
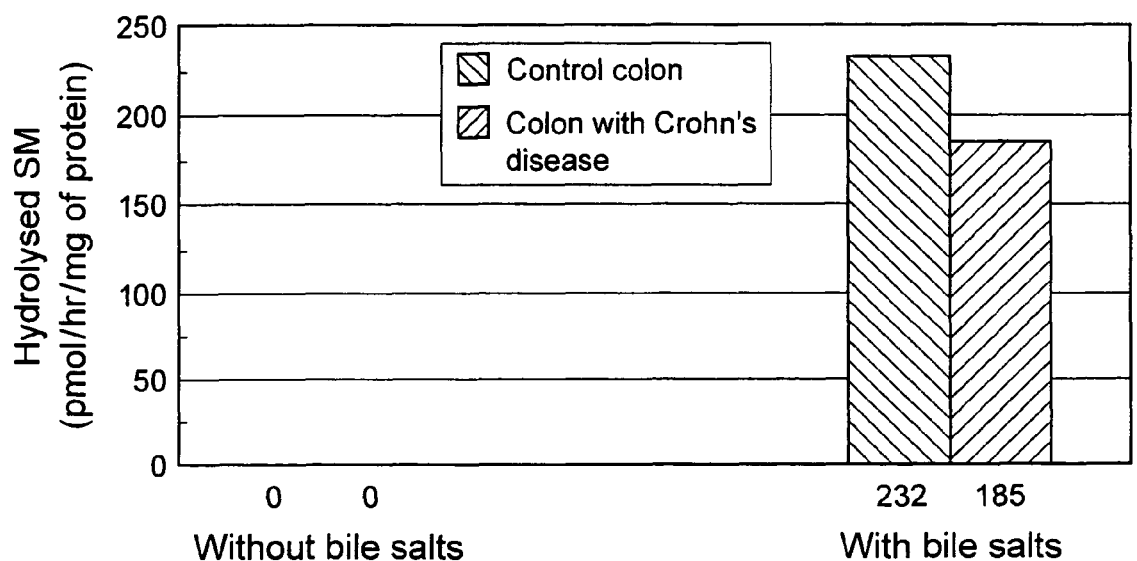
FIG. 2 is a graph showing alkaline SMase found in intestinal biopsy material.

FIG. 2 shows that the analysis of SMase activity in the intestinal biopsy samples showed a high activity of alkaline SMase of the kind dependent on bile salts, which could not be detected in the absence of bile salts. The levels of enzymatic activity in the tissues of a patient suffering from Crohn's disease showed a lower level of alkaline SMase than the control sample.

Effect of *Streptococcus thermophilus* on Intestinal Alkaline SMase

Figure 3:
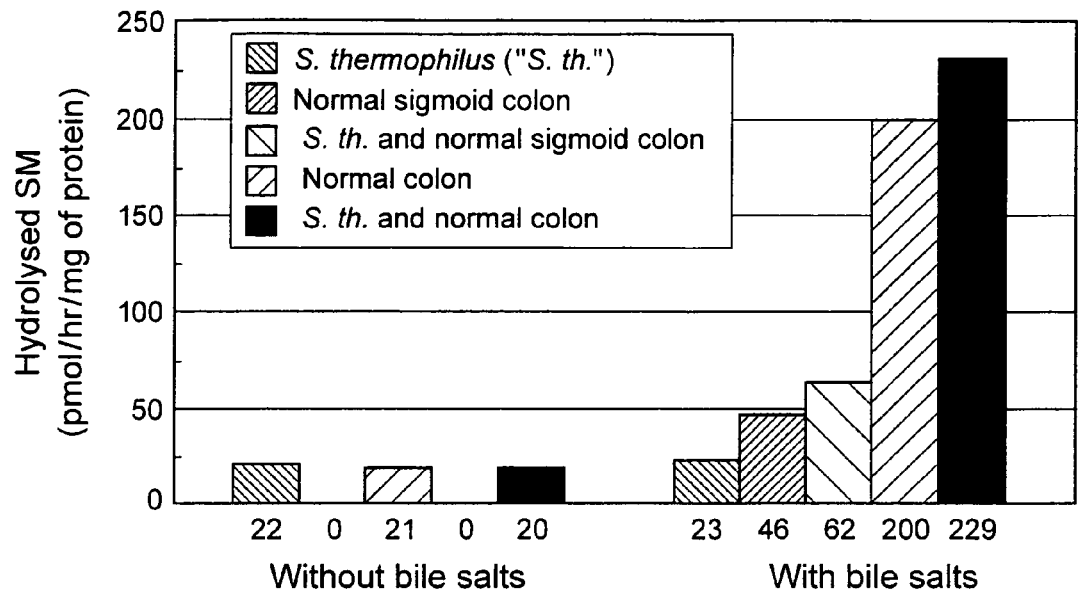
FIG. 3 is a graph showing an effect of *Streptococcus thermophilus* on intestinal alkaline SMase.

As shown in FIG. 3, the assay of the activity of SMase in the samples of *Streptococcus thermophilus*, under the experimental conditions used for the determination of intestinal SMase, showed that the bacterial enzyme was not affected by the presence or absence of bile salts. Furthermore, when the bacterial SMase activity and the intestinal SMase activity were tested simultaneously, the hydrolysis of SM increased additively. Similar results (not shown) were obtained with alkaline sphingomyelinase from the *Lactobacillus brevis* CD2 strain, filed on Feb. 6, 1998 under access No. DSM 11,988 in the German Collection of Microorganisms and Cell Cultures in Braunschweig, Germany ("Deutsche Sammlung von Mikroorganismen und Zellkulturen GmbH") under the Budapest Treaty, or mutants or derivatives thereof.

Treatment and Preventing Relapse of Pouchitis

Figure 4:
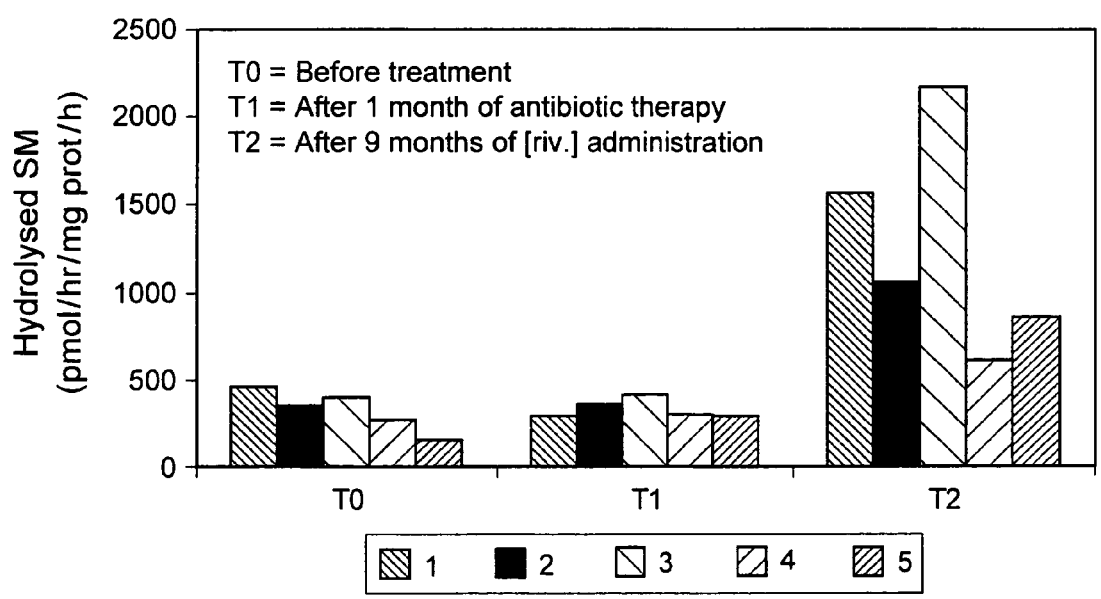
FIG. 4 shows the effect of a combination of lactic acid bacteria and bifidebacteria on intestinal alkaline SMase activity in pouchitis patients.

FIG. 4 shows the effect of a combination of lactic acid bacteria and bifidobacteria on intestinal alkaline SMase activity in pouchitis patients. Pouchitis is a nonspecific inflammation of the ileal reservoir and is the most common long-term complication after pouch surgery for ulcerative colitis. It is characterized by increased stool frequency, low-grade fever and extraintestinal manifestations may also occur. Pouchitis is presented here as an illustration of an inflammatory intestinal disorder and equates to an inflammatory and apoptosic processes of the intestine or an inflammatory intestinal disease.

Patients selected for the study were administered a mixture of the strains *Lactobacillus casei*, *Lactobacillus plantarum*, *Lactobacillus acidophilus*, *Lactobacillus delbrueckii*, *Bifidobacterium longum*, *Bifidobacterium breve*, and *Bifidobacterium infantis*. These strains are alkaline sphingomyelinase producers. Patients were selected, examined and administered the above mixture and assessed for pouchitis relapse following the procedures described in Gionchetti et al, Gasterenterology 2000;119:305-390 (the disclosure of which is hereby incorporated by reference). FIG. 4 is a histogram of the measured alkaline SMase activity in 5 pouchitis patients assessed by mucosal biopsy using the assay described in the above Methods section. Results are reported before treatment (T0), after 1 month of antibiotic (polymyxin and kanamycin) therapy (T1) and after nine months treatment with the above mixture of probiotic bacterial strains (T2). This together with other aspects of the study demonstrate the use of a mixture of strains of alkaline sphingomyelinase-producing probiotic bacteria significantly enhance the production of alkaline sphingomyelinase and are thereby useful in the treatment of chronic relapsing pouchitis.

Increase in Intestinal Alkaline Sphingomyelinase Levels via Food Supplement

Figure 5:
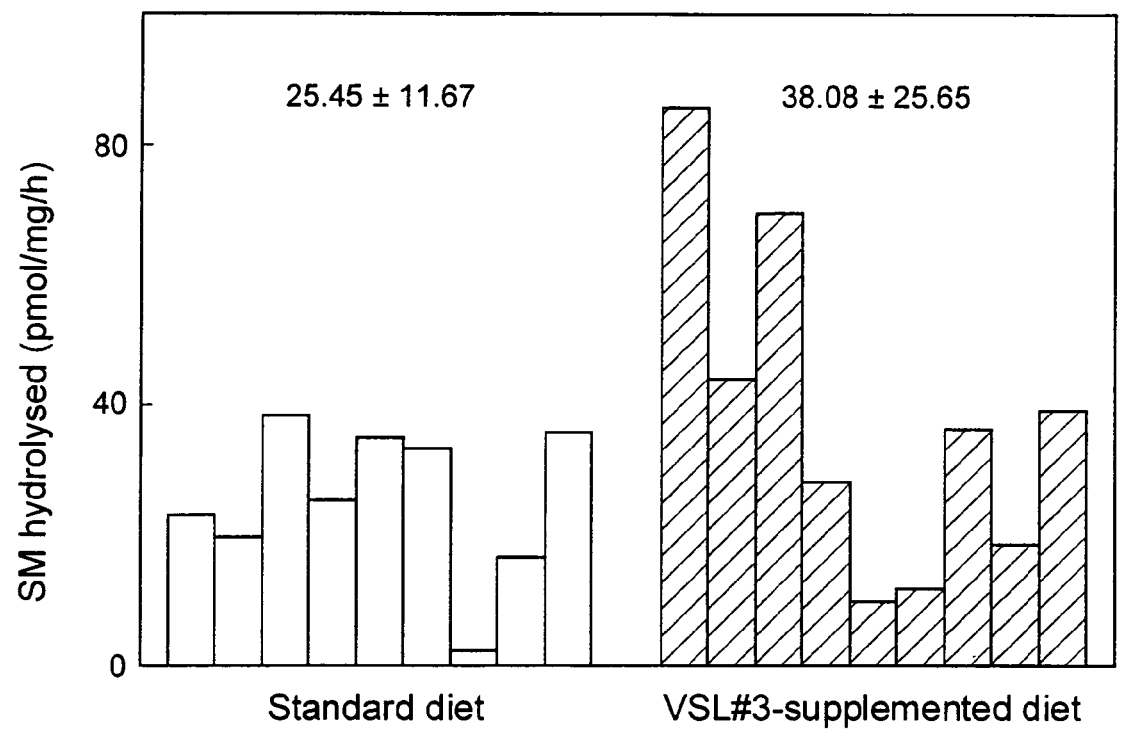
FIG. 5 shows the effect on alkaline SMase in animal (rat) tissue.

FIG. 5 shows the effect of on intestinal alkaline sphingomyelinase levels in rats with a diet supplemented with a mixture of the strains *Lactobacillus casei*, *Lactobacillus plantarum*, *Lactobacillus acidophilus*, *Lactobacillus delbrueckii*, *Bifidobacterium longum*, *Bifidobacterium breve*, and *Bifidobacterium infantis*.

The invention claimed is:

1. A dietetic, nutrient or pharmaceutical composition for oral, enteral or parenteral administration comprising:
    (a) a preparation comprising a bacterial extract comprising a sonicated alkaline sphingomyelinase-expressing bacterium; or
    (b) a preparation of lyophilized alkaline sphingomyelinase-expressing bacteria,
    wherein the bacterial extract preparation or the lyophilized bacterial preparation is formulated at between about $1 \times 10^2$ and about $200 \times 10^9$, $150 \times 10^9$ or $4 \times 10^9$ bacteria per gram of dietetic, nutrient or pharmaceutical composition,
    and the alkaline sphingomyelinase:
        hydrolyzes a sphingomyelin to a ceramide and a phosphorylcholine, and the hydrolysis is optimal at about pH 9, and
    the dietetic, nutrient or pharmaceutical composition is formulated for oral, enteral or parenteral administration.

2. The dietetic, nutrient or pharmaceutical composition of claim 1, further comprising or formulated as an artificial milk, a condensed milk, a soybean milk, a powdered milk, a partially humanized milk or a baby food.

3. The dietetic, nutrient or pharmaceutical composition of claim 1, wherein the bacterial extract of (a) is derived from a lactic acid bacterium, or the bacterium of (b) is a lactic acid bacterium.

4. The dietetic, nutrient or pharmaceutical composition of claim 3, wherein the lactic acid bacterium is from the *Lactobacillus brevis* CD2 strain, deposited on Feb. 6, 1998 under access No. DSM 11,988 in the German Collection of Microorganisms and Cell Cultures (DSM) in Braunschweig, Germany.

5. The dietetic, nutrient or pharmaceutical composition of claim 1, wherein the bacterial extract of (a) further comprises a live alkaline sphingomyelinase-expressing bacteria.

6. The dietetic, nutrient or pharmaceutical composition of claim 1, wherein the bacteria extract preparation or the lyophilized bacterial preparation is formulated to have between about $200 \times 10^9$ *Streptococcus thermophilus*, $150 \times 10^9$ *Bifidobacteria* and $4 \times 10^9$ *Lactobacillus acidophilus* per gram of dietetic, nutrient or pharmaceutical composition.

7. The dietetic, nutrient or pharmaceutical composition of claim 1, further comprising a bile acid, an ursodeoxycholic acid, a pectin, a sphingomyelin, an arginine deiminase, a fatty acid, a polyunsaturated fatty acid, a non fermented sugar, a lactulose, cholesterol inhibitor, a ceramidase inhibitor, a protease inhibitor, an immunomodulator, an anti-carcinogenic agent, a vitamin, a growth factor, a surfactant, a cereal, a fiber, an emulsifier, a stabilizer, a lipid, an antioxidant, a preservative, a free-radical neutralizer, a vasoprotector or mixtures thereof.

8. The dietetic, nutrient or pharmaceutical composition of claim 1, in a form suitable for enteral alimentation administration.

9. The dietetic, nutrient or pharmaceutical composition of claim 1, in a form suitable for pediatric administration.

10. The dietetic, nutrient or pharmaceutical composition of claim 1, in the form of a food supplement.

11. The dietetic, nutrient or pharmaceutical composition of claim 1, wherein the bacterial extract of (a) comprises a supernatant prepared by a method comprising:
 (a) providing an alkaline sphingomyelinase-expressing bacterium;
 (b) suspending the bacterium;
 (b) sonicating the suspended bacterium; and
 (c) obtaining a supernatant comprising the alkaline sphingomyelinase.

12. The dietetic, nutrient or pharmaceutical composition of claim 1, wherein the bacterial extract of (a) is prepared from one or more of, or the lyophilized bacteria of (b) comprise one or more of: a *Lactobacillus acidophilus, Lactobacillus brevis, Lactobacillus buchneri, Lactobacillus casei, Lactobacillus catenaforme, Lactobacillus cellobiosus, Lactobacillus crispatus, Lactobacillus curvatus, Lactobacillus delbrueckii, Lactobacillus fermentum, Lactobacillus jensenii, Lactobacillus leichmannii, Lactobacillus minutus, Lactobacillus plantarum, Lactobacillus rogosee, Lactobacillus salivarius, Bifidobacterium adolescentis, Bifidobacterium angulatum, Bifidobacterium bifidum, Bifidobacterium breve, Bifidobacterium catenulatum, Bifidobacterium dentium, Bifidobacterium eriksonii, Bifidobacterium infantis, Bifidobacterium longum, Bifidobacterium plantarum, Bifidobacterium pseudocatenulatum, Bifidobacterium pseudolongum, Streptococcus lactis, Streptococcus raffinolactis* or a *Streptococcus thermophilus*.

13. A food supplement comprising an alkaline sphingomyelinase in the form of:
 (a) a bacterial extract comprising a sonicated alkaline sphingomyelinase-expressing bacterium; or
 (b) a lyophilized alkaline sphingomyelinase-expressing bacterium,
 wherein the bacterial extract preparation or the lyophilized bacterial preparation is formulated at between about $1 \times 10^2$ and about $200 \times 10^9$, $150 \times 10^9$ or $4 \times 10^9$ bacteria per gram of food supplement,
 and wherein:
 the alkaline sphingomyelinase hydrolyzes a sphingomyelin to a ceramide and a phosphorylcholine, and the hydrolysis is optimal at about pH 9.

14. The food supplement of claim 13, wherein the bacterial extract preparation or the lyophilized bacterial preparation is formulated to have between about $200 \times 10^9$ *Streptococcus thermophilus*, $150 \times 10^9$ *Bifidobacteria* and $4 \times 10^9$ *Lactobacillus acidophilus* per gram of food supplement.

15. The dietetic, nutrient or pharmaceutical composition of claim 1, wherein the alkaline sphingomyelinase is in the form of a bacterial extract comprising a sonicated alkaline sphingomyelinase-expressing bacterium.

16. The dietetic, nutrient or pharmaceutical composition of claim 1, wherein the alkaline sphingomyelinase is in the form of a lyophilized alkaline sphingomyelinase-expressing bacterium.

17. The food supplement of claim 13, wherein the alkaline sphingomyelinase is in the form of a bacterial extract comprising a sonicated alkaline sphingomyelinase-expressing bacterium.

18. The food supplement of claim 13, wherein the alkaline sphingomyelinase is in the form of a lyophilized alkaline sphingomyelinase-expressing bacterium.

19. The food supplement of claim 13, wherein the bacterial extract is derived from a lactic acid bacterium, or the bacterium is a lactic acid bacterium.

20. The food supplement of claim 19, wherein the lactic acid bacterium is from the *Lactobacillus brevis* CD-2 strain, deposited on Feb. 6, 1998 under access No. DSM 11,988 in the German Collection of Microorganisms and Cell Cultures (DSM) in Braunschweig, Germany.

21. The dietetic, nutrient or pharmaceutical composition of claim 1, wherein the bacterial extract of (a) is prepared from one or more of, or the lyophilized bacteria of (b) comprise one or more of: a *Lactobacillus casei*, a *Lactobacillus plantarum*, a *Lactobacillus acidophilus*, a *Lactobacillus delbrueckii*, a *Bifidobacterium longum*, a *Bifidobacterium breve*, and a *Bifidobacterium infantis*.

22. The food supplement of claim 19, wherein the bacterial extract of (a) is prepared from one or more of, or the lyophilized bacteria of (b) comprise one or more of: a *Lactobacillus casei*, a *Lactobacillus plantarum*, a *Lactobacillus acidophilus*, a *Lactobacillus delbrueckii*, a *Bifidobacterium longum*, a *Bifidobacterium breve*, and a *Bifidobacterium infantis*.

* * * * *